United States Patent [19]

Smyczek et al.

[11] Patent Number: 5,100,775
[45] Date of Patent: Mar. 31, 1992

[54] METHOD FOR CONDUCTING NUCLEIC ACID HYBRIDIZATION IN CHAMBER WITH PRECISE FLUID DELIVERY

[76] Inventors: Peter J. Smyczek, 1837 N. Himount Blvd., Milwaukee, Wis. 53208; John A. Thompson, 2908 Ward Kline Rd., Myersville, Md. 21771

[21] Appl. No.: 491,587

[22] Filed: Mar. 12, 1990

Related U.S. Application Data

[62] Division of Ser. No. 168,994, Mar. 16, 1988, Pat. No. 4,908,319.

[51] Int. Cl.$^5$ .............................. C12Q 1/68
[52] U.S. Cl. .......................... 435/6; 436/87; 935/78
[58] Field of Search .............. 435/6, 284, 285, 287, 435/288, 289; 436/807; 935/78

[56] References Cited

U.S. PATENT DOCUMENTS

| | | | |
|---|---|---|---|
| 2,143,585 | 1/1939 | Stein | 422/102 X |
| 2,439,572 | 4/1948 | Levin | 422/102 X |
| 3,540,985 | 4/1971 | Gross | 435/298 X |
| 3,591,461 | 7/1971 | Bazil et al. | 435/298 |
| 3,591,480 | 7/1971 | Neff et al. | 435/288 X |
| 3,843,324 | 10/1974 | Edelman et al. | 422/101 X |
| 4,052,163 | 10/1977 | Patzner | 422/101 |
| 4,087,327 | 5/1978 | Feder et al. | 435/285 X |
| 4,090,850 | 5/1978 | Chen et al. | 422/102 X |
| 4,288,316 | 9/1981 | Hennessy | 422/101 X |
| 4,301,010 | 11/1981 | Eddleman et al. | 422/101 X |
| 4,493,815 | 1/1985 | Ferwood et al. | 422/101 |
| 4,557,899 | 12/1985 | Schoonouea et al. | 422/102 X |
| 4,634,676 | 1/1987 | Sapafino | 435/298 X |
| 4,642,220 | 2/1987 | Bjorkman | 435/300 X |
| 4,681,852 | 7/1987 | Handy et al. | 435/285 X |
| 4,786,474 | 11/1988 | Cooper | 422/102 X |
| 4,797,259 | 1/1989 | Matkovich et al. | 422/102 X |

*Primary Examiner*—David L. Lacey
*Assistant Examiner*—Jan M. Ludlow
*Attorney, Agent, or Firm*—James N. Videbeck

[57] ABSTRACT

An improved method for carrying out multiple laboratory processes including hybridization, cell growth and chromatographic separations including steps of: providing a laboratory apparatus having a hollow recessed chamber and a removable cover sized to be slidably retained in at least a portion of the hollow recessed chamber for providing a variable volume chamber. Inserting a sandwich including a membrane having DNA fragments bound thereto, and a porous non-reactive filter on either side of the membrane into the chamber and inserting the slidable cover, a distance sufficient to provide a minimum volume chamber for the sandwich. Delivering a pre-hybridization solution to the chamber by utilizing a fluid administration kit in fluid communication with the chamber and pre-hybridizing the DNA fragments at a desired temperature. Removing the pre-hybridization solution from the chamber by the fluid administration kit. Delivering a probe/hybridization solution to the chamber by the fluid administration kit and hybridizing the DNA fragments at the same temperature as pre-hybridization. Removing the hybridization solution from the chamber by the fluid administration kit. Passing a low salt wash fluid through the chamber by the fluid administration kit to wash the DNA containing membrane. Then removing the cover from the hollow recessed chamber, and remove the membrane from the chamber and allow the membrane to dry.

2 Claims, 3 Drawing Sheets

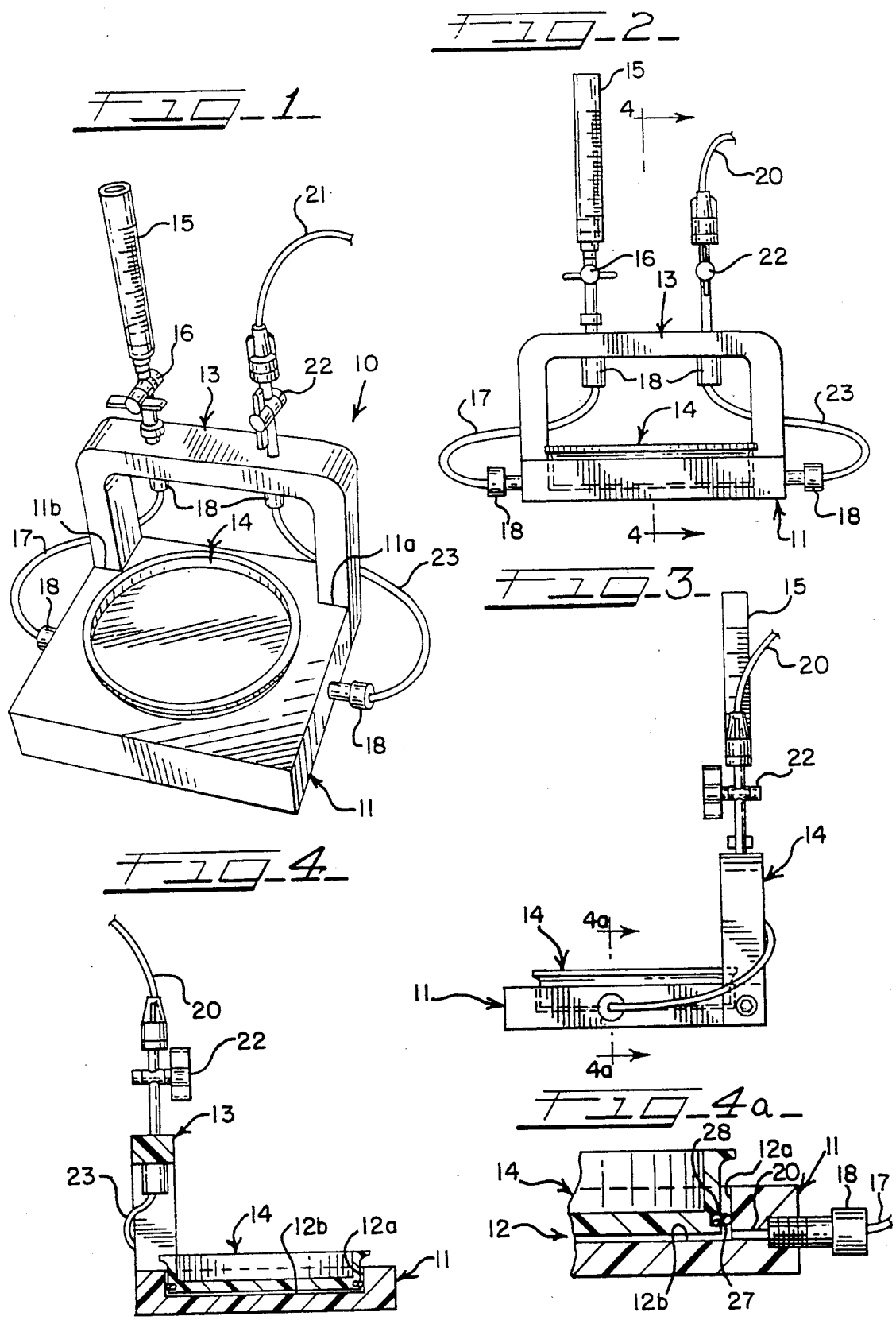

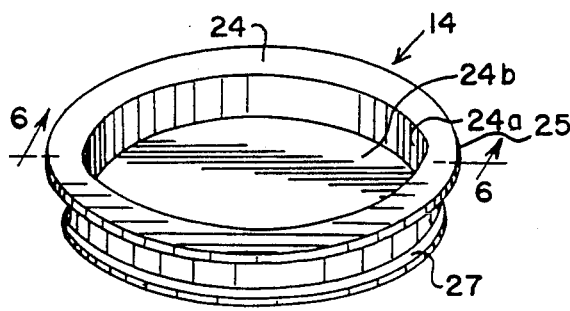
FIG-5-
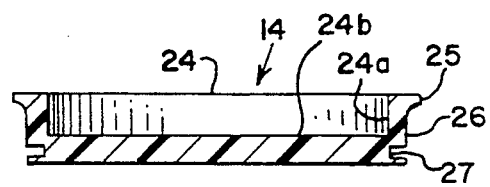
FIG-6-
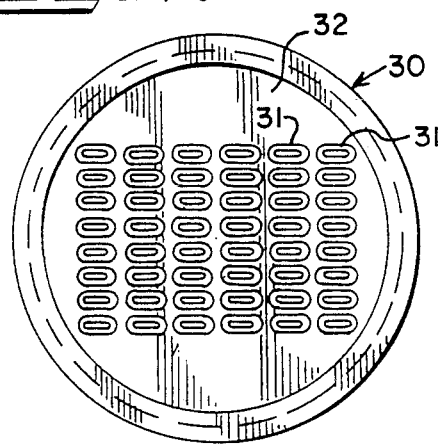
FIG-7a-
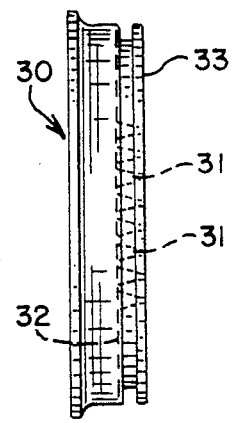
FIG-7b-
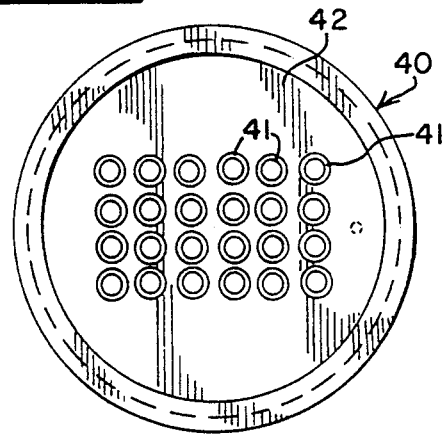
FIG-8a-
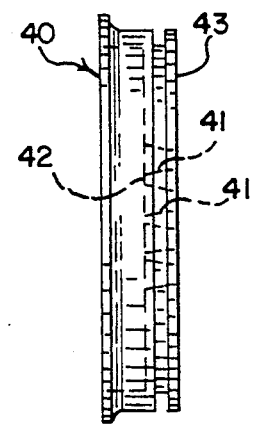
FIG-8b-

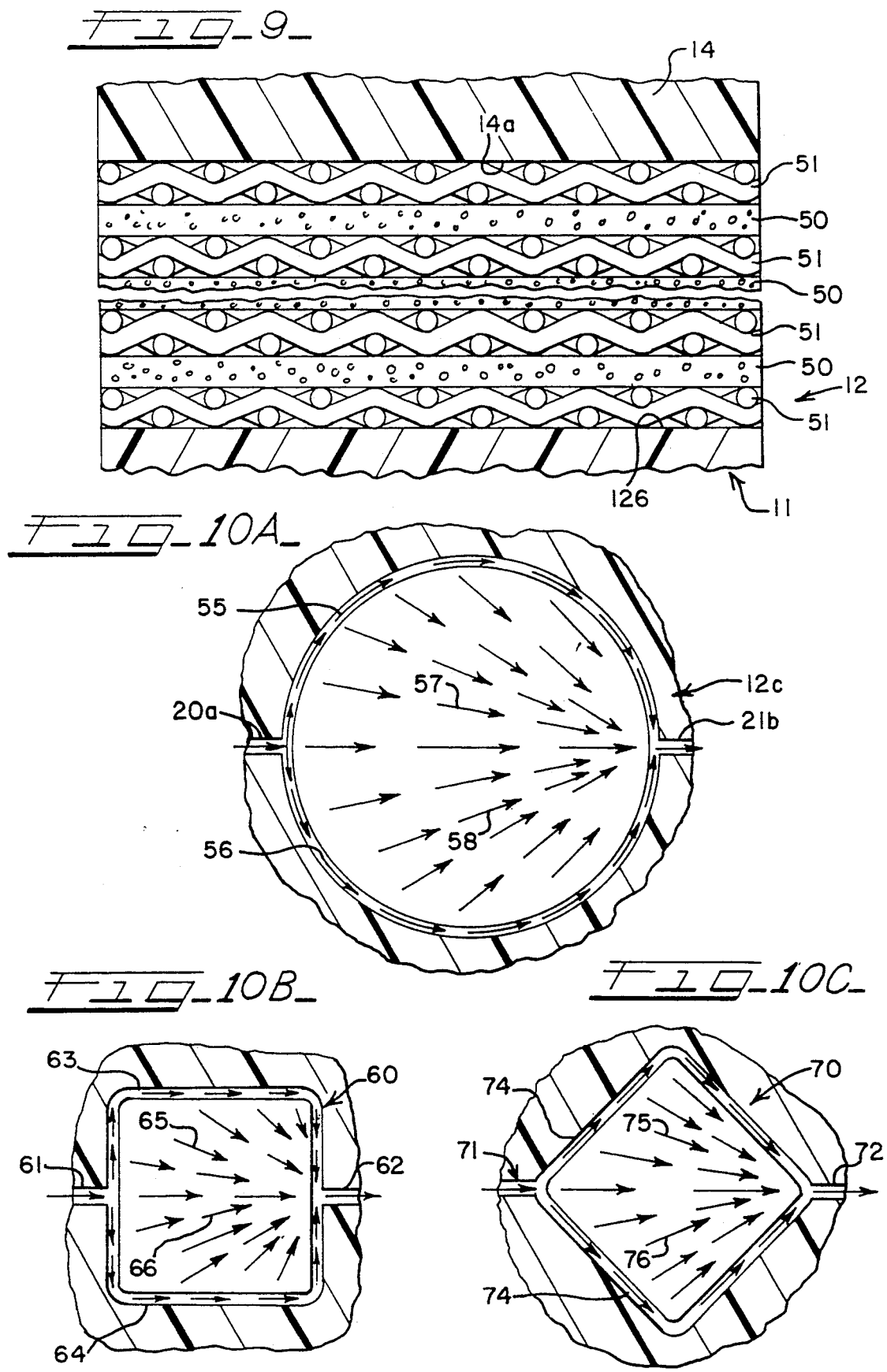

METHOD FOR CONDUCTING NUCLEIC ACID HYBRIDIZATION IN CHAMBER WITH PRECISE FLUID DELIVERY

This is a divisional of co-pending application Ser. No. 168,994 filed on Mar. 16, 1988, now U.S. Pat. No. 4,908,319.

BACKGROUND OF THE INVENTION

This invention relates to equipment and procedures for carrying out micro-biological tests and experiments, and more particularly, to an apparatus for growing cells, conducting hybridization analysis, and extracting chromatographic separations.

Prior to the present invention, hybridization processes were carried out in selectable re-sealable plastic bags. Solutions, filters and membranes would be placed in the plastic bag and sealed, and the bag placed in a water bath for temperature monitoring. Cell culture growth has been carried out in cylindrical roller bottles utilizing microcarrier beads or hollow fibers on which to deposit cultures to be grown. Chromatography techniques have utilized glass tube columns, or thin papers dipped in a mixture for capillary action.

Needs have developed for a single improved laboratory apparatus which not only provides for exacting and efficient use of hybridization solutions in a small, minimum volume, highly controlled chamber, but also provides like chambers for growth of cell cultures, and chambers through which particles may be separated by differing rates of flow therethrough.

Therefore, it is an object of the present invention, generally stated, to provide a single improved laboratory apparatus capable of being used for a multitude of separate activities presently being performed in differing type apparatus.

SUMMARY OF THE INVENTION

The invention defines an apparatus for conducting laboratory processes and comprises a chamber base member having a substantial horizontal orientation with a low profile for efficient temperature control when used with a conventional water bath. The base member including a hollow recessed chamber extending downwardly from an opening at a top of the base member. The chamber is one of a generally rectangular and a generally cylindrical shape and is sized to receive standard laboratory accessories, such as filters, membranes, or the like. The chamber further includes substantially diametrically opposed input and output bores positioned adjacent the bottom of the chamber in fluid communication with same.

The apparatus further includes a low profile chamber cover member being generally shallow in height and sized for being snuggly slidably received in the recessed hybridization chamber. Annular sealing means are positioned around the outside of the cover for sealingly engaging the cover in the chamber recess when it is positioned over the chamber. A sliding sealed engagement between the chamber cover and the chamber recess in the base member defines a variable sized chamber adapted for receiving and processing variable numbers of laboratory accessories therein.

Handle means extend outwardly of a plane of the low profile base member for aiding manual grasping and moving of the apparatus by a user.

BRIEF DESCRIPTION OF THE DRAWINGS

The features of the present invention which are believed to be novel are set forth with particularity in the appended claims. This invention, together with further objects and advantages thereof, may best be understood by reference to the following detailed description taken in conjunction with the accompanying sheets of drawings, in the several features of which like reference numerals identify like elements, and in which:

FIG. 1 is a perspective view of the laboratory apparatus constructed in accordance with the present invention;

FIG. 2 is a front elevational view of the laboratory apparatus shown in FIG. 1;

FIG. 3 is an end elevational view of the laboratory apparatus of the present invention;

FIG. 4 is a cross-sectional view taken substantially along lines 4—4 of FIG. 2;

FIG. 4a is a fragmentary enlarged cross-section along one side of the chamber taken along line 4a—4a of FIG. 3;

FIG. 5 is a perspective view of the removable chamber cover shown in FIG. 1;

FIG. 6 is a cross-sectional view taken substantially along lines 6—6 of FIG. 5;

FIG. 7a is a top plan view of a modification of the laboratory chamber cover for making the apparatus suitable for use as a slot blot unit;

FIG. 7b is an end elevational view of the modification of the laboratory chamber cover shown in FIG. 7a;

FIG. 8a is a top plan view of a second modification of the laboratory chamber cover for making the apparatus suitable for use as a dot blot unit; and FIG. 8b is an end elevational view of the second modification of the laboratory chamber cover shown in FIG. 8a;

FIG. 9 is an enlarged fragmentary elevational sectional view of the laboratory chamber having filters sandwiched therein;

FIG. 10a is a diagrammatic view of a fluid flow path through a cylindrical laboratory chamber of the invention;

FIG. 10b is a diagrammatic view of one fluid flow path through a square laboratory chamber of the invention;

FIG. 10c is a diagrammatic view of a second fluid flow path through a square laboratory chamber of the invention.

DETAILED DESCRIPTION OF THE PREFERRED EMBODIMENT

Referring to FIGS. 1 through 4a, a laboratory chamber apparatus, generally indicated at 10, constructed in accordance with the present invention, includes a rectangular base, generally indicated at 11. A hollow, shallow (and in this embodiment) cylindrical recessed chamber 12 extends downwardly from the top center of base 11 defining a concave cylindrical sidewall 12a. A generally flat circular bottom wall 12b encloses the bottom of sidewall 12a and a U-shaped handle 13 is affixed at each of its opposed distal ends to a notched cut out 11a–11b at opposing sides of one end of the base 11. Fluid administration apparatus including a syringe 15, a petcock or valve 16 positioned at the base of syringe 15, and a plastic fluid carrying line 17 extends through two of a plurality of hollow threaded type mountings 18—18 with one on handle 13, and the other on the side of base 11, respectively, to a capillary type channel 20 (FIG. 4a) in base 11 which is in fluid communication with chamber 12 at the juncture of the sidewall 12a and the bottom 12b thereof. On the opposite side of handle 13 is a second fluid administration apparatus denoted by a vacuum or faucet aspirator line 21, a second petcock 22 a second flexible plastic tubing 23 which extends through two more of the hollow threaded mounting 18—18 in the handle 13 and the opposing side of base 11, respectively, which likewise is connected to a second capillary channel (not shown) which is in communication with the opposing side of chamber 12 from capillary channel 20 shown in FIG. 4a similarly thereto.

As shown most clearly in FIGS. 1, 5 and 6, a disc shape cover, indicated generally at 14, is adapted to sealingly fit into and over the hollow cylindrical recess or chamber 12, and includes a top surface 24 which preferably includes a shallow hollow cylindrical recess thereon defined by vertical sidewall 24a and a flat surface 24b across the base of sidewall 24a. The outer portion of the cover top surface 24 includes a radially extending flange 25 which is undercut to join with cover cylindrical sidewall 26 while providing a leverage area for manual removal of the cover 14 from the laboratory chamber recess 12. Upwardly adjacent the flat bottom 14a of the cover 14 on sidewall 26 is positioned an annular recess 27 for providing a mounting for an O-ring seal 28 (FIG. 4a) which sealingly engages the cover 14 over the chamber recess 12

The preferred material for the laboratory apparatus is acrylic plastic which protects users from beta particles emitted by probes used in some hybridization procedures. The diameter of chamber 12 is standardized at preferred dimensions of 82 mm and 138 mm in order to facilitate the use of standard size round filters and membranes, etc. The chamber may also be made in other standard laboratory shapes, such as square, etc., (see FIGS. 10b, 10c) as long as two dimensions of the chamber are fixed, and the third dimension is preferably variable.

The chamber cover 14 of the invention may have a flat top surface, or may include a recessed top surface 24. The recess in the top surfaces cuts down on the overall weight of the cover 14 and provides a lowered, flat operational surface for additional modifications to be discussed below. The bottom surface 14a of cover 14 forms the upper surface of the chamber 12. The ability of cover 14 to move up and down so as to vary and minimize the volume of chamber 12 allows DNA hybridization, culture growth, and chromatography work to take place while using a minimum amount of the various necessary solutions in the chamber. The 82 mm size uses just 2 ml of solution to wet the system plus 0.4 ml per filter (see FIG. 9). The 138 mm size wets with 5.5 ml of solution plus 1.2 ml per filter disc.

Thus, an improved laboratory chamber has been shown and described which may be used for numerous differing laboratory operations, such as amplifying nucleic acid sequences present in a nucleic acid, growing cells on large surface area objects placed in the chamber, separating the constituents of a mixture in the chamber by running fluid through the mixture, and the like.

Referring to FIG. 7a and 7b, a first modification of the cover 14 of FIG. 5 is generally indicated at 30. Cover 30 is configured identically to cover 14 with the exception that a plurality, in this embodiment 48, of elongate slots 31—31 are positioned in the center of cover 30 and extend from the inner top surface 32 of the cover through the cover to the bottom surface 33 thereof. Each slot 31 is slightly beveled or tapered so as to have a larger hollowed out area adjacent the top of the cover 30 than at the bottom 33 thereof. Each of the elongate holes or apertures 31—31 allows instruments to be positioned therein so as to deposit materials through the cover and onto membranes (not shown) positioned in the chamber for use in slot blot hybridization experiments.

Referring to FIGS. 8a and 8b, a second modification of the cover 14 of FIG. 5 is generally indicated at 40. Cover 40 is identical to cover 14 with the exception that it includes a plurality, in this embodiment 24, of apertures 41—41 positioned in the central part of the cover and extending from the inner top surface 42 thereof through the cover to the bottom surface 43 thereof. The apertures 41—41 are round in horizontal cross section and slightly beveled or tapered so as to have a larger hollowed out area adjacent the top of the cover 42 than at the bottom surface 43 thereof. Each of the round holes 41—41 allows instruments to be positioned therein similarly to that noted above in connection with the first modification 30 of cover 14. Experiments carried on with cover 40 are termed dot blot hybridization experiments.

As shown most clearly in the diagram of FIG. 9 when the chamber 12, which is the area between chamber base 12b and the bottom surface 14a of chamber cover 14, is in use it may likely be filled by a porous multi layered sandwich structure consisting of alternating layers of thin porous membranes, 50—50 or other solid phase material on which desired proteins, molecules, cells, or the like, may be positioned, and alternating layers of woven porous filter material 51—51. In the applications for which apparatus 10 is presently utilized, the purpose of the apparatus is to facilitate interaction between a fluid substance and a solid substance. The fluid substance would either be static or standing still in the chamber 12, or would be fluid in motion across the solid (nitro cellulose) membranes 50, or the like. Interaction between the liquid and solid phases is facilitated by the fine screen or mesh filters 51—51, which surround each membrane 50, and are preferably made of nylon or polypropylene mesh which would not interfere with the desired reactions taking place between the liquid and solid substances.

One advantage of the present apparatus 10 of the invention is that the number of liquid and solid phases utilized in any one testing apparatus may be increased or decreased as desired by the user, as the moveable chamber cover 14, when sealingly engaged on chamber base 11 over the desired numbers of filters 51 and substrates 50, provides a minimum volume chamber for whatever desired quantity of processing the user selects. As mentioned previously, liquids may be forced into the chamber by syringe 15, or pump or drawn through the chamber by vacuum lines 21, 23.

In hybridization, DNA fragments are separated on gels and denatured. Then the fragments are transferred from the gel to the membranes 50—50 by known procedures. A sandwich of membranes and filters on either side thereof are placed in the chamber and sealingly covered. A pre-hybridization solution is then added to the chamber by syringe 15 for a predetermined period of time, usually three hours to overnight, at a desired temperature, preferably between 37° C. and 42° C.

After pre-hybridization, which reduces non-specific hybridization with the probe substance, the prehybridization is removed through vacuum lines 20, 23. The membrane 50 with DNA fragments thereon is hybridized to the desired radio labelled nucleic acid probe. In this operation the probe/hybridization solution is added to the chamber by syringe 15 after the pre-hybridization solution is removed. The materials in the chamber are hybridized for a desired length of time, usually six hours to overnight, at the same temperatures used in pre-hybridization. After hybridization, the probe/hybridization solution is removed through vacuum lines 20,23 and the membranes 50—50 are washed in low salt washers while still in the chamber until examination with a Geiger counter indicates most of the membranes 50—50 read at background level. The washing of the filters and membranes removes unbound and weakly binding probe. The membranes 50 are then dried and auto radiographed.

In applications where cell cultures are to be grown, in one case animal cells grow in suspension or are attached to a solid support, depending on the type of cell and the culture conditions. Referring to FIG. 9, the cells may be grown on the micro-porous membranes 50—50 and with the filters 51—51 providing for a high level of culture medium (the liquid phase) contact with the cells to be grown in the chamber. Growth of cells on the microporous membranes 50—50 may be conducted with the liquid being stationary, or with the liquid circulating. Once the cells which have attached to the membranes 50—50 are sufficiently grown, the culture medium may be removed from the chamber, and another fluid medium, which is capable of detaching the cells from the membranes 50 may be introduced into the chamber and used to wash the grown cells from the chamber, where they may be later trapped and isolated. While cell cultures may be grown on porous membranes 50, they may be also grown on micro carrier means (not shown) having a large surface area on which the cells may attach, or they may also be grown on hollow fiber systems which may be contained in the chamber 12 in the laboratory apparatus 10 of the present invention.

The laboratory apparatus 10 of the present invention has also been found to be useful in separating mixtures by means of chromatography. A fluid carrying any mixture to be separated is allowed to flow through the chamber with its solvent over the surface of the membrane 50. Differing components of the mixture flow at differing rates, eventually becoming separated from each other by depositing themselves at differing positions along the fluid path on membrane 50. One use of chromatography is to break down a protein into the specific amino acids of which it is constructed. The apparatus 10 of the present invention has been shown to be an efficient means of separating mixtures of materials, including the amino acids making up a protein. The various amino acids separate out as those individual acids have differing flow rates in the medium. When separated, those materials deposit themselves on the membrane in clumps or clusters where they may be separated and removed.

Referring now to FIG. 10a, the flow path of a liquid medium through the thin cylindrical chamber 12 of the preferred embodiment of the invention shown in FIG. 1 is diagramatically shown. Fluid flows into the chamber through capillary passageway 20a and thence into the chamber 12c where it is first drawn around the circumferential boundary of the chamber as shown by pathways 55 and 56. As the fluid is pushed or drawn toward chamber exit 21b, it takes the path of least resistance, and portions of the fluid begin flowing across the open interior of the chamber, as denoted by fluid paths 57–58, toward the capillary outlet 21b of the chamber. The liquid path shown in FIG. 10a distributes the liquid throughout the chamber.

As shown in FIG. 10b, a modification of the preferred embodiment of the invention utilizes a square or rectangular chamber, generally indicated at 60, having capillary inlet port 61 and capillary outlet port 62 positioned mid way along the lengths of opposing sides of chamber 60 Fluid flowing through the inlet port 61 first attempts to traverse the chamber 60 by sticking to the square boundary or outside of the chamber 60 as indicated by arrows 63—64. However, as with the liquid in FIG. 10a, the liquid takes the path of least resistance and begins to separate from the boundary path and head across the open chamber toward the outlet port 62, as indicated by flow path arrows 65-66.

FIG. 10c shows a diagram of a flow path through a square chamber 70 having inlet ports 71 and outlet port 72 positioned at opposing corners of the chamber. As with the previous flow path, fluid flowing through inlet port 71 first attempts to traverse the chamber 70 by travelling along the chamber boundary as denoted by arrows 73 and 74. However, as the liquid is traversing along that path the fluid is also is inclined to take the path of least resistance toward outlet tube 72, and portions of the fluid begin to flow from where ever they are along the boundary path in a straight line toward the outlet tube, as denoted by flow path arrows 75—75.

Thus, an improved laboratory apparatus having a multitude of applications, and a multitude of modifications for carrying out those differing applications has been shown and described. It will be obvious to those skilled in the art that additional changes may be made without departing from the invention in its broader aspects. Therefore the aim of the appended claims is to cover all such changes and modifications as fall within the true spirit and scope of the invention.

The invention is claimed as follows:

1. A method for conducting nucleic acid hybridization utilizing a laboratory chamber apparatus comprising the steps of:

providing a chamber base member having a substantially horizontal orientation with a low profile for efficient temperature control when used with a conventional water bath, said base member including a hollow recessed chamber extending downwardly from an opening at a top of said base member, said chamber being fixed in shape at least with respect to length and width, said chamber further including input and output bores positioned adjacent the bottom of said chamber at substantially opposed positions and being in fluid communication with said chamber.

providing a low profile chamber cover member being generally shallow in height and sized and shaped for being slidably received in said hollow recessed chamber, said chamber cover member having annular sealing means positioned on the outside of said chamber cover member for sealingly engaging said recessed chamber when positioned through said opening thereof, wherein said chamber cover member slidably received in said recessed chamber defines a variable height chamber adapted for receiving and processing at least one membrane therein, and providing fluid administration means on said apparatus and in fluid communication with at least one of said inlet and outlet bores for precise movement of fluids as desired into and out of said chamber, inserting a sandwich including a membrane having DNA fragments bound thereto and a porous non-reactive filter on either side of said membrane into said chamber, inserting said chamber cover member into said recessed chamber in sealed relation therewith a distance sufficient to provide a minimum volume chamber for said sandwich therein, delivering a pre-hybridization solution to said chamber by said fluid administration means and pre-hybridizing said DNA fragments at a desired temperature, removing pre-hybridization solution from the chamber by said fluid administration means.

delivering a probe/hybridization solution to said chamber by said fluid administration means and hybridizing said DNA fragments at the same temperature as the pre-hybridization step, removing the hybridization solution from the chamber by said fluid administration means, passing a low salt wash fluid through said chamber by said fluid administration means to wash the DNA containing membrane, and removing said cover from said hollow recessed chamber, and removing said membrane from said chamber and allowing the membrane to dry.

2. An improved method for carrying out multiple laboratory processes including hybridization, cell growth and chromatographic separations comprising the steps of:

providing a laboratory apparatus having a hollow recessed chamber therein and a removable cover sized to be slidably retained in at least a portion of said hollow recessed chamber for providing a variable volume for said chamber;

inserting a sandwich including a membrane having DNA fragments bound thereto, and a porous non-reactive filter on either side of said membrane into said chamber, inserting said chamber cover member into said recessed chamber in sealed relation therewith a distance sufficient to provide a minimum volume chamber for said sandwich therein, delivering a pre-hybridization solution to the chamber by utilizing a fluid administration means in fluid communication with said chamber and pre-hybridizing said DNA fragments at a desired temperature;

removing the pre-hybridization solution from the chamber by said fluid administration means;

delivering a probe/hybridization solution to said chamber by said fluid administration means and hybridizing said DNA fragments at the same temperature as the pre-hybridization step;

removing the hybridization solution from the chamber by said fluid administration means;

passing a low salt wash fluid through said chamber by said fluid administration means to wash the DNA containing membrane; and removing said cover from said hollow recessed chamber, and removing said membrane from said chamber and allowing the membrane to dry.

* * * * *